(12) United States Patent
Pedros et al.

(10) Patent No.: US 8,333,780 B1
(45) Date of Patent: Dec. 18, 2012

(54) SURGICAL TOOL AND METHOD OF OPERATION

(75) Inventors: Roberto Pedros, Oxford, CT (US); Scott Reed, Monroe, CT (US); Pete Wilson, Killingworth, CT (US)

(73) Assignee: Okay Industries, Inc., New Britain, CT (US)

( * ) Notice: Subject to any disclaimer, the term of this patent is extended or adjusted under 35 U.S.C. 154(b) by 218 days.

(21) Appl. No.: 12/794,303

(22) Filed: Jun. 4, 2010

Related U.S. Application Data

(60) Provisional application No. 61/184,422, filed on Jun. 5, 2009.

(51) Int. Cl.
*A61B 17/32* (2006.01)

(52) U.S. Cl. .......................................... 606/174; 600/37

(58) Field of Classification Search .................... 606/79, 606/167, 174, 205, 206; 600/37, 562, 572
See application file for complete search history.

(56) References Cited

U.S. PATENT DOCUMENTS

| | | | |
|---|---|---|---|
| 5,792,135 A | 8/1998 | Madhani et al. | |
| 5,954,692 A | 9/1999 | Smith et al. | |
| 6,206,903 B1 * | 3/2001 | Ramans | 606/205 |
| 6,554,844 B2 | 4/2003 | Lee et al. | |
| 6,676,684 B1 | 1/2004 | Morley et al. | |
| 6,685,698 B2 | 2/2004 | Morley et al. | |
| 6,840,938 B1 | 1/2005 | Morley et al. | |
| 6,843,793 B2 | 1/2005 | Brock et al. | |
| 6,949,106 B2 | 9/2005 | Brock et al. | |
| 6,991,627 B2 | 1/2006 | Madhani et al. | |
| 7,214,230 B2 | 5/2007 | Brock et al. | |
| 2007/0255109 A1 | 11/2007 | Stein et al. | |
| 2008/0058861 A1* | 3/2008 | Cooper et al. | 606/205 |
| 2008/0119870 A1 | 5/2008 | Williams | |
| 2008/0221391 A1 | 9/2008 | Weitzner et al. | |
| 2008/0228196 A1 | 9/2008 | Wang et al. | |

FOREIGN PATENT DOCUMENTS

WO   96/10957 A1   4/1996

* cited by examiner

*Primary Examiner* — Victor Nguyen
(74) *Attorney, Agent, or Firm* — Cantor Colburn LLP

(57) ABSTRACT

A surgical tool and method of operation are provided. The surgical tool includes an end effector, such as a surgical scissor. The end effector is coupled to an actuating mechanism having a clevis and a pulley. A cable engages the pulley and is attached to one side of the clevis. When one portion of the cable is pulled, the clevis is moved in a first direction causing the end effector to open. When a second portion of the cable is pulled, the clevis moves in the opposite direction and the end effector is closed. The system also includes a mechanism for changing the orientation of the end effector. Another embodiment includes a mechanism for actuating the cable and the end effector.

17 Claims, 20 Drawing Sheets

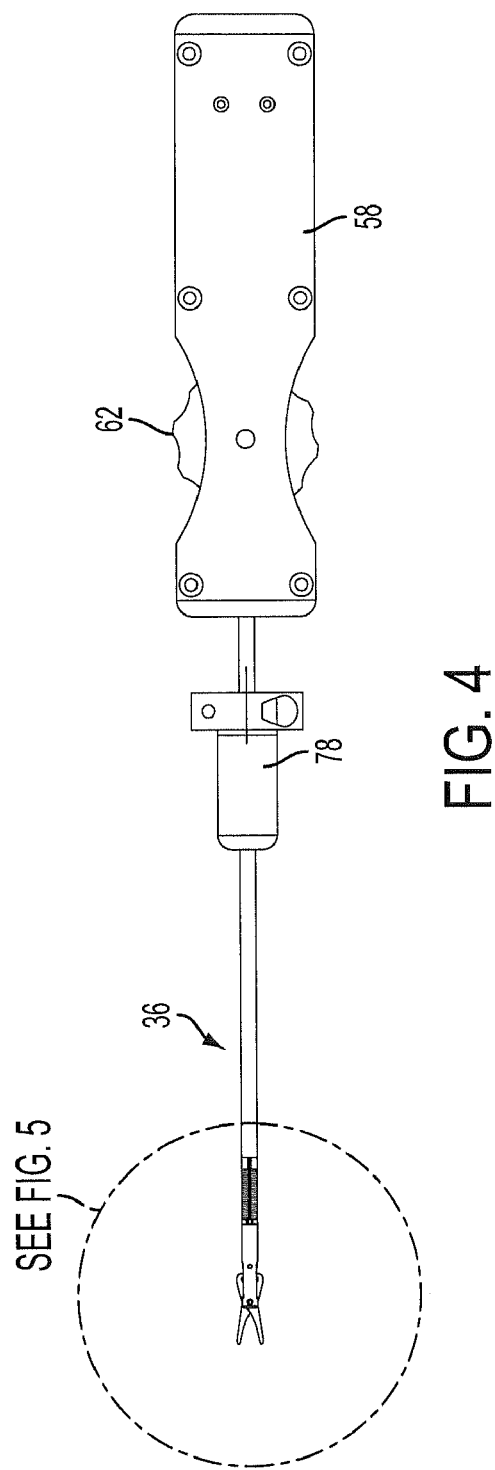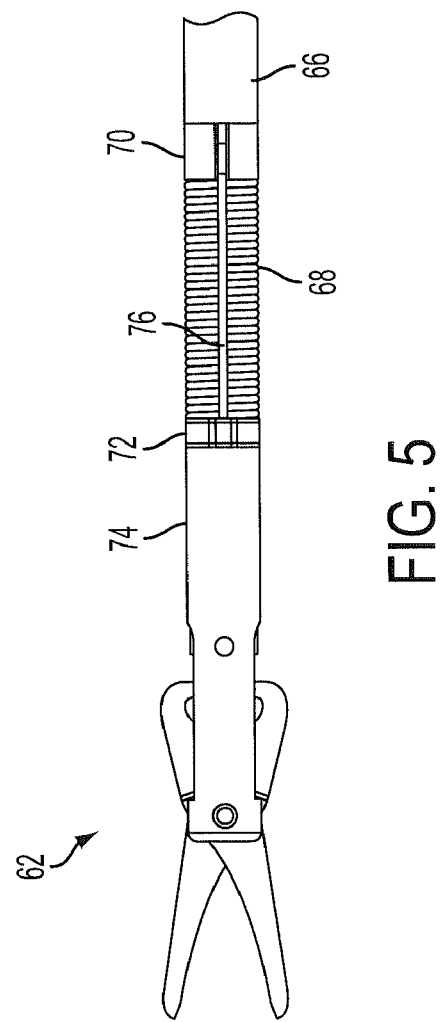

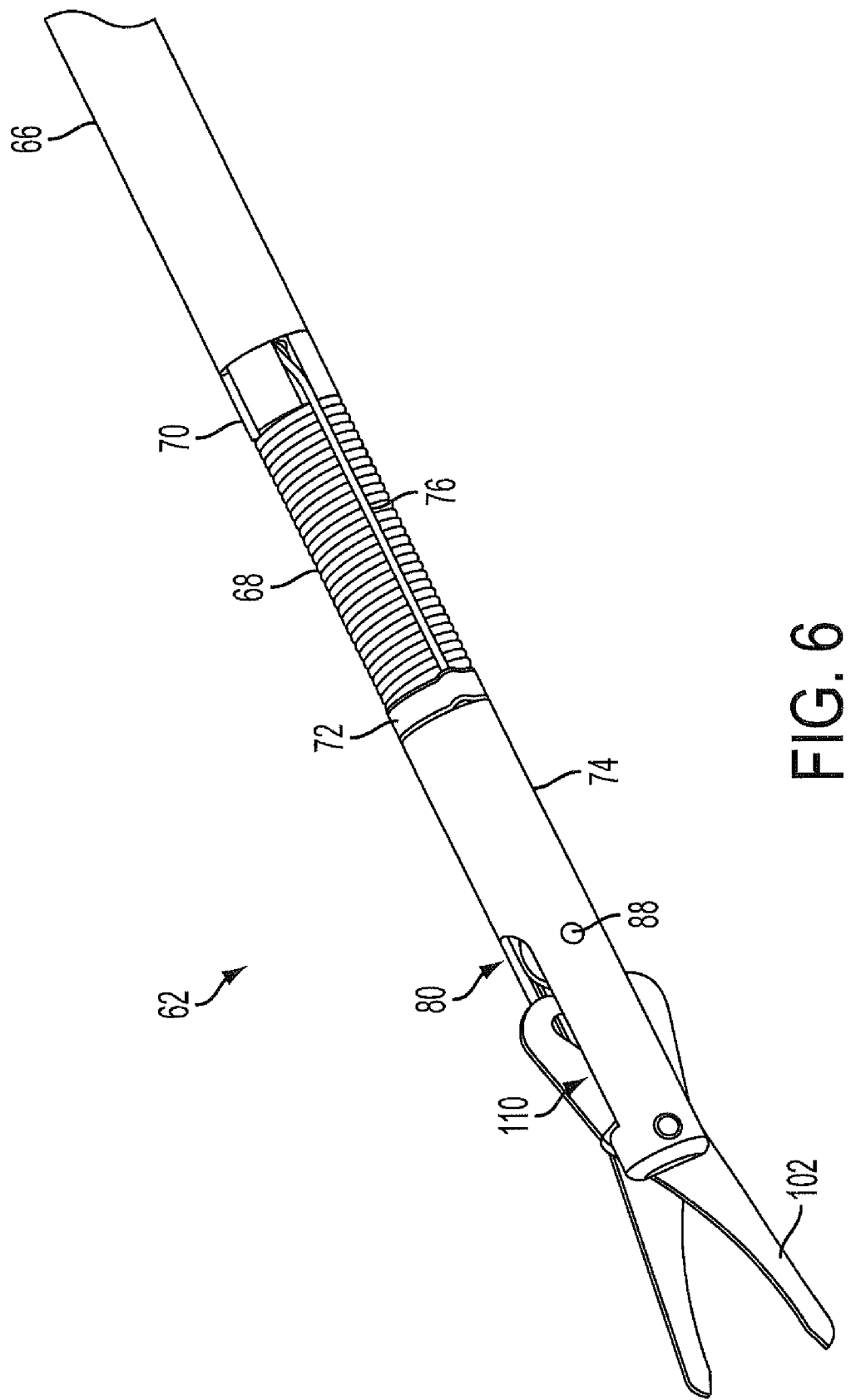

SURGICAL TOOL AND METHOD OF OPERATION

BACKGROUND OF THE INVENTION

The present invention relates generally to a device for assisting with a medical procedure and, more specifically, to a device that may be directly actuated by a surgeon, or used in conjunction with a robotic surgery system.

Minimally invasive surgical procedures have gained increased acceptance within the medical community. These procedures, sometimes referred to as laparoscopic, endoscopic, arthroscopic or keyhole surgery for example, use several small incisions to provide the surgeon access to the areas of the patient requiring attention. These incisions are small, typically on the order of 0.5 cm-1.5 cm. The surgeon uses a camera to view the surgical area and control tools or implements during the operation. These implements include tools such as cameras, forceps, cutters or dissectors for example. A device known as a trocar is often used in the incision during the procedure to allow the insertion and removal of the implements during the surgery. Minimally invasive procedures provide a number of benefits in reducing risks of infection and increasing the patient's time period for recovery.

The minimally invasive procedures may be performed either manually or through some type of robotic apparatus. In a manual procedure, the surgeon directly holds the surgical implement during the surgery. This allows the surgeon to act directly through the tool to perform the necessary repairs to the patient. One advantage of this method is that the surgeon receives some tactile feedback by holding the tool. Manual procedures also provide additional advantages in cost, setup time and speed of operation.

Minimally invasive surgical procedures are also performed using robotic systems. The robotic apparatus has two discrete and usually separate portions, a control center for the surgeon and a surgical machine adjacent the operating table. The surgeon views the patient through a video display that can be actively manipulated by the surgeon to change or enhance the view, such as by changing angles or magnifying critical areas for example. Sensors are attached to the surgeon by a sleeve over the surgeon's arm, and/or with gloves or some type of gripper. A computer system receives electrical signals from the sensors and translates them into movements of motors and linkages on the surgical machine. This allows surgical instruments to move in response and mimic the movements performed by the surgeon. An assistance team provides support to the surgeon during the procedure and performs tasks such as preparing the patient, changing instruments and caring for the patient when the procedure is complete. Robotic surgical apparatus provide a number of advantages. While the control center and the surgical machine are typically located proximate to each other, this does not necessarily need to be the case. The control center could be located at a center location where specialized medical personnel reside, while the surgical machine may be located in a remote village, or in the military application, next to a battlefield for example. This allows for highly complex surgical procedures to be performed over a wide area with only a few doctors. Further, since the robotic surgical machine provides a high degree of control and precision, the robotic system can also facilitate procedures that typically cannot be performed manually.

Still other systems have been proposed that combine the cost and tactile feedback benefits of manual endoscopic procedures with the precision and control of the robotic surgical machine. These systems, sometimes referred to as direct drive systems, use a rail platform and a guide sheath that accepts multiple endoscopic instruments. The system is mounted to the operating table, or adjacent to on a freestanding frame, in close proximity to the patient. Handles or actuators are then provided to allow the surgeon control of the implements. The handles are directly coupled via cables and linkages to the endoscopic instruments. This allows the surgeon to directly manipulate the instruments and since there is a physical connection (e.g. no computer) between the patient and the surgeon, a limited amount of tactile feedback is transmitted to the surgeon.

It should be appreciated that no matter what type of system is used, size is an important parameter for endoscopic instruments. The smaller the instrument, the smaller the incision and the lower the risk of infection. Further, the smaller the instrument, the more instruments can be fitted within a standard size incision. Advantages can be gained by increasing the number of instruments since the need to change instruments during the procedure will be reduced. This reduces the chances of the patient being inadvertently injured during the withdrawal or insertion of the instruments.

Typically, endoscopic instruments have an over all length of 30 cm-150 cm with an instrument having a length of 4 mm-5 mm and a diameter of 2 mm-4 mm. In the case of instruments such as forceps, scissors, dissectors, or graspers for example, the instrument also needs to be operated between an open and closed position. These instruments also need to articulate about two axes, rotating to an angle relative to the axis of the instrument, and also rotating about the axis of the instrument. This functionality is performed by arrangements utilizing multiple pulleys and cables and/or push rods. It should be appreciated that the mechanisms required to both operate and articulate instrument tend to increase the size of the instrument.

Accordingly, while existing surgical tools are suitable for their intended purposes, there still remains a need for improvements. In particular, improvements are needed regarding the operation of the surgical tools that are operated between positions during the surgical procedure, while also reducing the size and complexity of the surgical tool.

SUMMARY OF THE INVENTION

In one embodiment of the invention, a surgical tool is provided having an end effector. The end effector includes a first pivot and an operable portion on a first side of the first pivot. The end effector also includes a slot on a second side opposite the first pivot. A clevis is slidably coupled to the slot. A pulley is arranged adjacent the second side. A cable is coupled to one side of the clevis adjacent the pulley and engaging the pulley.

In another embodiment, a surgical tool is provided having a handle. A first actuator is coupled for rotation to the handle. A first cable is operably coupled to the actuator. A clevis having a first side is coupled to the first cable, the clevis being slidable between a first position and a second position. A pulley is arranged adjacent to the clevis opposite the handle, the pulley engaging the first cable. An end effector device is operably coupled to the clevis.

In yet another embodiment, a method of operating a surgical tool is provided. The method includes the step of moving a first portion of a cable in a first direction about a pulley. A clevis is moved in a second direction in response to the cable first portion being moved in the first direction. A first end effector portion is rotated in a third direction with the clevis in response to the cable first portion being moved in the first direction. A second end effector is rotated in a fourth direction with the clevis in response to the cable first portion being moved in the first direction.

BRIEF DESCRIPTION OF THE DRAWINGS

Referring now to the drawings, which are meant to be exemplary and not limiting, and wherein like elements are numbered alike:

FIG. 4 is a side plan view illustration of the surgical tool of FIG. 3;

FIG. 5 is a partial side view illustration of the surgical tool of FIG. 4;

FIG. 6 is a partial perspective view illustration of the surgical tool of FIG. 5;

DETAILED DESCRIPTION

Figure 1:
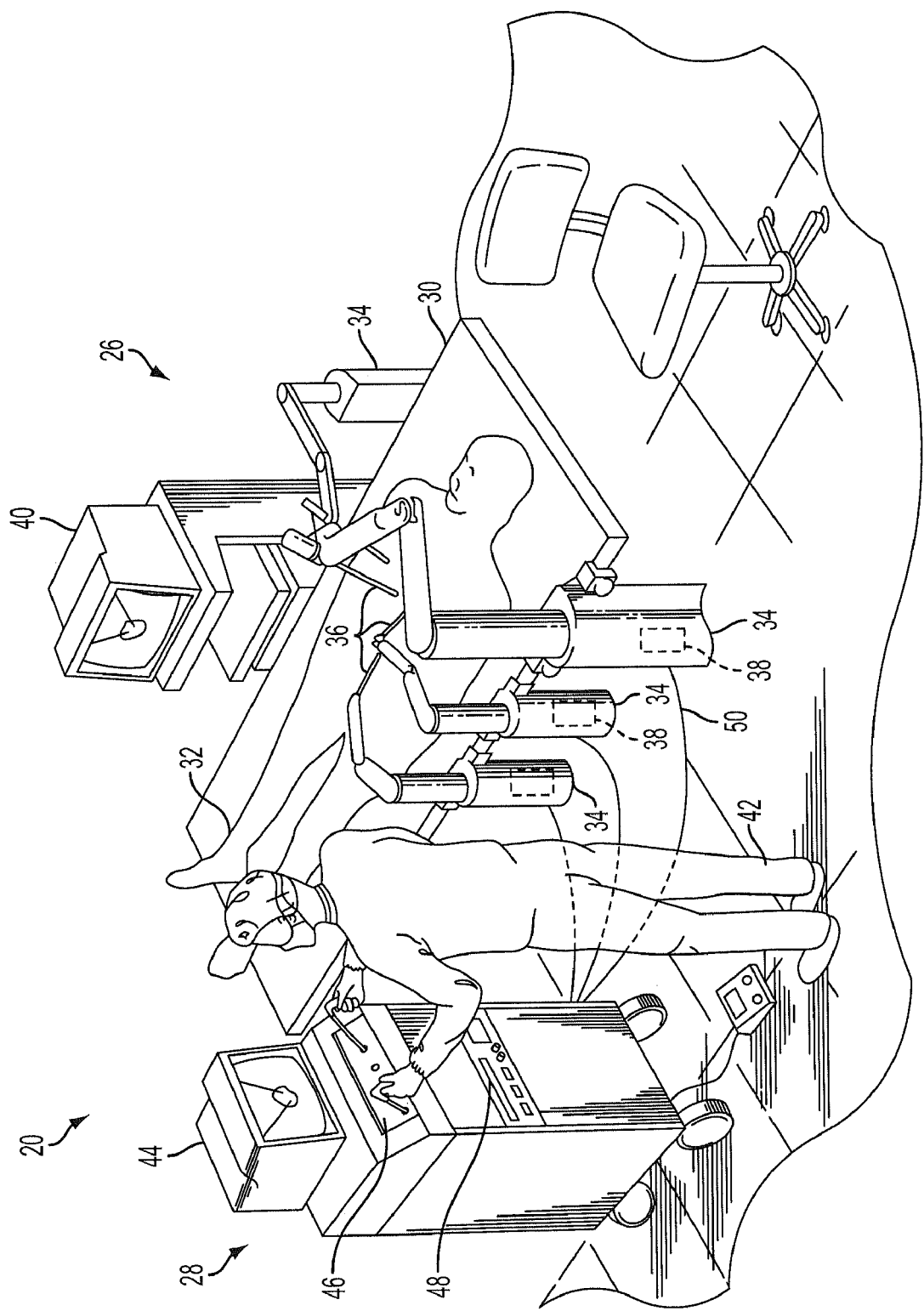
FIG. 1 is a perspective view illustration of a robotic surgical system in accordance with one embodiment of the invention.
Figure 2:
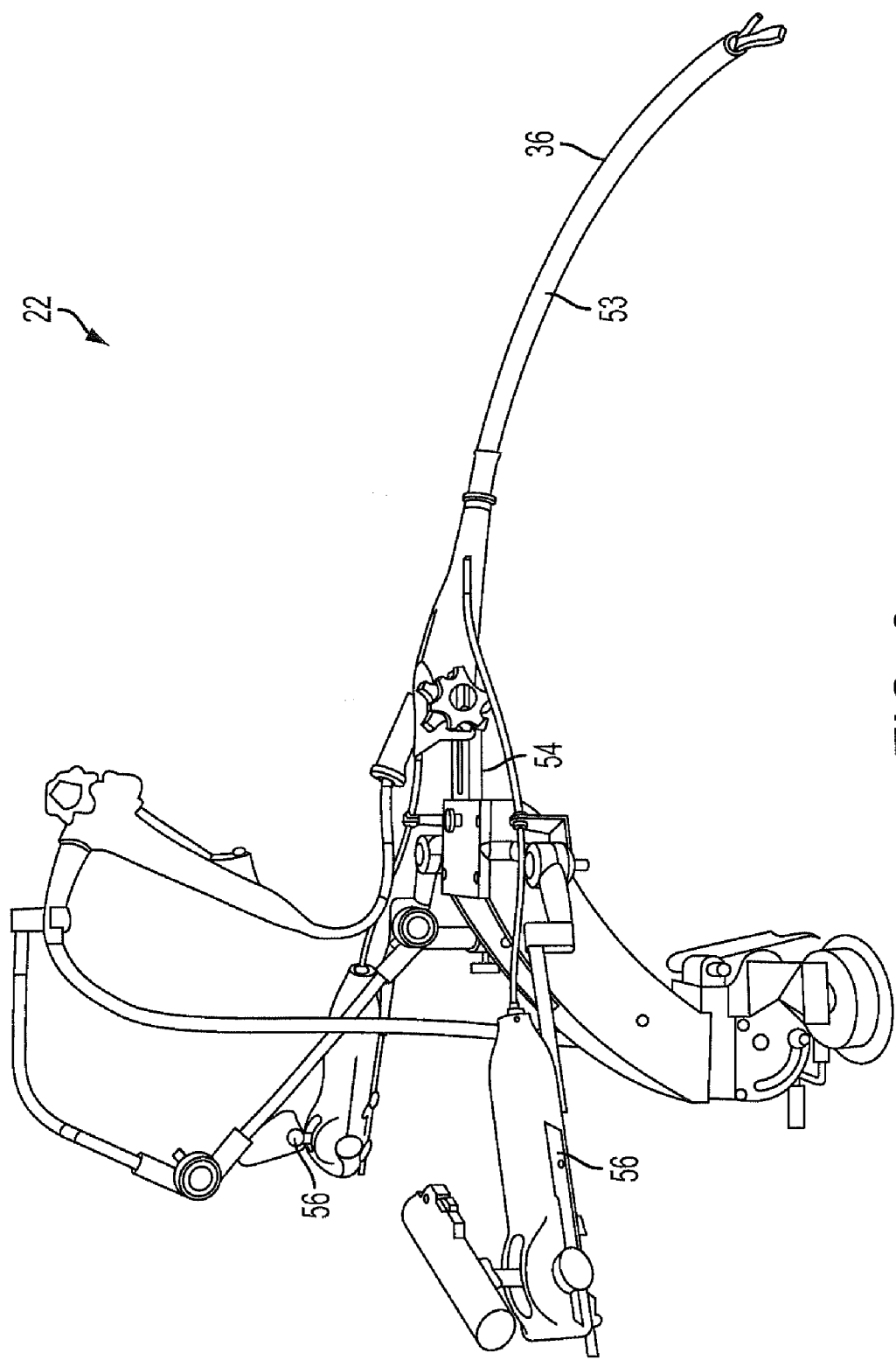
FIG. 2 is a perspective view illustration of a direct drive surgical system in accordance with one embodiment of the invention.
Figure 3:
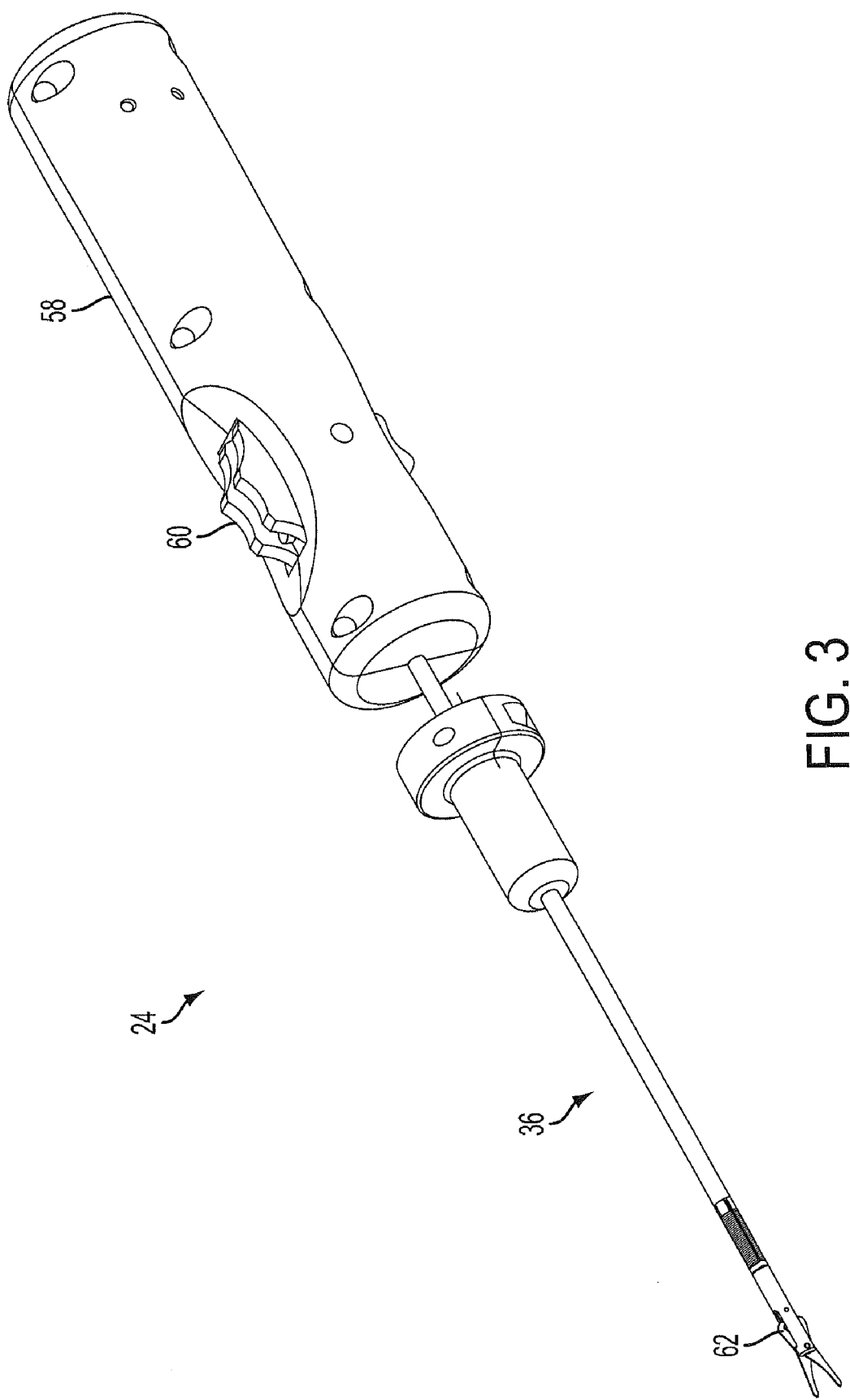
FIG. 3 is a perspective view illustration of a hand-held surgical tool in accordance with one embodiment of the invention.

FIGS. 1-3 illustrate exemplary embodiments of surgical systems 20, 22, 24 that assist surgeons in performing minimally invasive medical procedures. The first embodiment is a robotic type surgical system 20. The robotic surgical system 20 includes an operating table unit 26 and a remote control unit 28. It should be appreciated that while the remote control unit 28 is illustrated as being disposed adjacent the operating table unit 26, this is merely for illustration purposes and the control units 26, 28 may also be located in geographically distant areas. The operating table unit 26 includes a platform 30 upon which the patient 32 rests during the procedure. Attached to the platform 30 is one or more surgical apparatus 34 that includes a plurality of surgical tools 36. The surgical apparatus 34 also includes an actuator or motor 38 that is coupled to move and articulate the surgical tools 36. The operating table unit 26 may also include one or more monitors 40 that may be used by the surgeon 42 or their support assistance team during the procedure.

The surgeon 42 uses the remote control unit 28 to move and manipulate the surgical tools 36 and thus perform the desired medical procedure. The remote control unit 28 typically includes a monitor 44 that displays images acquired by a camera coupled to the surgical apparatus 34. It should be appreciated that one of the surgical tools 36 may be a camera. A control interface 46 is provided to allow the surgeon to interact with the surgical tools 36. A computer system 48 interprets the surgeon's 42 manipulations of the control interface 46 and transmits signals over one or more communications mediums 50 that connect the control unit 28 to the operating table unit 26. The communications medium 50 allows the signals from the control interface 46 to be transferred to the surgical apparatus 34. It should be appreciated that the communications medium 50 may be a wired medium, a wireless medium, an optical medium, or a combination of the foregoing. The robotic system 20 provides advantages in allowing a remotely located surgeon to perform complex medical procedures on a patient.

A direct drive surgical system 22 is illustrated in FIG. 2. The direct drive system 22 is similar to the robotic system 20 in that the surgeon manipulates the surgical tools 36 through a set of mechanical linkages 52. In the direct drive system 22, the surgical tool 36 may be positioned within a sheath 53. The surgical tool 36 and the sheath 53, are coupled to a rail system 54 that in turn is supported by a patient platform or freestanding frame (not shown). The rail system 54 supports the surgical tool 36 and interfaces the surgical tool 36 with the control devices 56. The control devices 56 allow the surgeon to move, rotate and actuate the surgical tools 36. It should be appreciated that the direct drive system 22 may also includes a monitor (not shown) that allows the surgeon to view images acquired by a camera that is also inserted through the sheath 53. The direct drive system 22 provides a direct mechanical connection between the patient and the surgeon allowing for the use of minimally invasive techniques while also providing some tactile feedback to the surgeon.

The third embodiment is a manual hand held surgical system 24 illustrated in FIG. 3. This embodiment includes a surgical tool 36 that is directly coupled to a handle 58 having an actuation knob 60. In this embodiment, the surgeon holds the surgical system 24 without the assistance of any support frames or devices. As will be discussed in more detail below, the surgical tool portion 36 includes an end effector 62 that the surgeon uses to perform procedures within the patient. As used herein, the end effector 62 may include, but is not limited to scissors, forceps, graspers, punches and fan style retractors for example. During the medical procedure, the surgeon inserts the end effector 62 through an incision and directly manipulates the orientation, position and angle of the end effector 62. The surgeon uses the actuation knob 60 to control the position and state of the end effector 62. As will be discussed below, in some embodiments a mechanical arrangement is provided to rotate the end effector 62 relative to the longitudinal axis of the surgical tool 36. It should be appreciated that the hand-held system 24 provides advantages in the speed and cost over the robotic system 20 and the direct drive system 22 in that the manual surgical system 24 is simpler and therefore less costly to manufacture. Further, since less patient and operating room preparation is required, a surgeon may more quickly initiate a medical procedure.

For purposes of clarity, the end effector 62, the tool portion 36 and the actuation mechanism 64 (FIG. 11) are discussed in reference to the hand-held system surgical embodiment. However, it will be appreciated by those skilled in the art that the actuation mechanism 64, the tool portion 36 and the end effector 62 may be readily used in either the direct drive system 22 or the robotic system 20 without deviating from the scope of the claimed invention. In the case of the robotic system 20, the force for actuating the actuation mechanism 64 may come from electromechanical devices such as a motor or a solenoid for example.

Referring now to FIGS. 4-10, the tool portion 36 and the end effector 62 will be discussed. The end effector 62 includes a shaft 74 that is coupled to a sheath 66 by a flexible member 68. In the exemplary embodiment, the sheath 66 is substantially ridged, made from a material such as 316 stainless steel for example. A pair of termination tips 70, 72 adapt the flexible portion 68 to the shaft 74 and the sheath 66. As will be discussed in more detail below, the termination tip 72 is coupled to a cable 76 that connects the termination tip 72 to a collar 78. In response to the collar 78 being moved, the cable causes the flexible member 68 to bend and rotate the orientation of the end effector 62 relative to the sheath 66. In the exemplary embodiment, the flexible member 68 is a spring.

The shaft 74 includes an inner bore 80 that houses a clevis 82 having a pair of arms 84. Each arm 84 includes a slot 86 that is sized to receive a pin 88. The pin 88 is coupled to the shaft 74. The slots 86 are sized to allow the clevis 82 to slide freely over the pin 88. The clevis 82 further includes a body portion 90 having a pair of grooves 92, 93. The grooves 92, 93 extend the length of the body portion and are aligned with a pulley 94 coupled to pin 88. The grooves 92, 93 are further sized to receive an actuator cable 96 that extends from the handle 58 and engages the pulley 94. In the exemplary embodiment, the actuator cable 96 is attached to the groove 92, such as by welding or adhesive bonding for example, such that there is no relative motion between the actuator cable 96 and the groove 92.

A pin 98 extends between the ends of the clevis arms 84. As will be described in more detail below, the pin 98 interacts with slots 100 on the end effector device 102. It should be appreciated that while the end effector device 102 is illustrated and referred to herein as a scissor 102, the end effector device 102 may be any surgical implement having rotary motion that is used in minimally invasive surgery, such as laparoscopic, endoscopic or arthroscopic surgery for example. As such, the end effector device 102 may be, but is not limited to, scissors, forceps, graspers, punches and fan style retractors for example. The scissors 102 are retained to the shaft 74 by a pin 104. The pin 104 allows the scissors 102 to rotate between an open (FIG. 9) and a closed (FIG. 10) position.

The scissors 102 include a blade portion 106 on one side of the pivot pin 104 and an actuation portion 108 on the opposite side of pin 104. The actuation portion 108 includes the slots 100. In the exemplary embodiment, the slots 100 are arranged on an angle relative to the centerline of the clevis 82. The actuation portions 108 are positioned within the bore 80 and extend into an opening 110 in the shaft when the scissors are moved to the open position (FIG. 6). In the exemplary embodiment, the scissors 102 are arranged to pivot about the pin 104 and slide over each other creating a shearing force on an object as the scissors are moved from the open to the closed position.

It should be appreciated that while embodiments herein describe the end effector 62 and the scissors 102 as having two moving arms, the claimed invention should not be so limited. In other embodiments, the end effector 62 may have one arm and a means of fixating the pulley 94 to the arm rather than being position between the two arms. Similarly, it is contemplated that the end effector 62 may have a one fixed and one movable arm.

Figure 9:
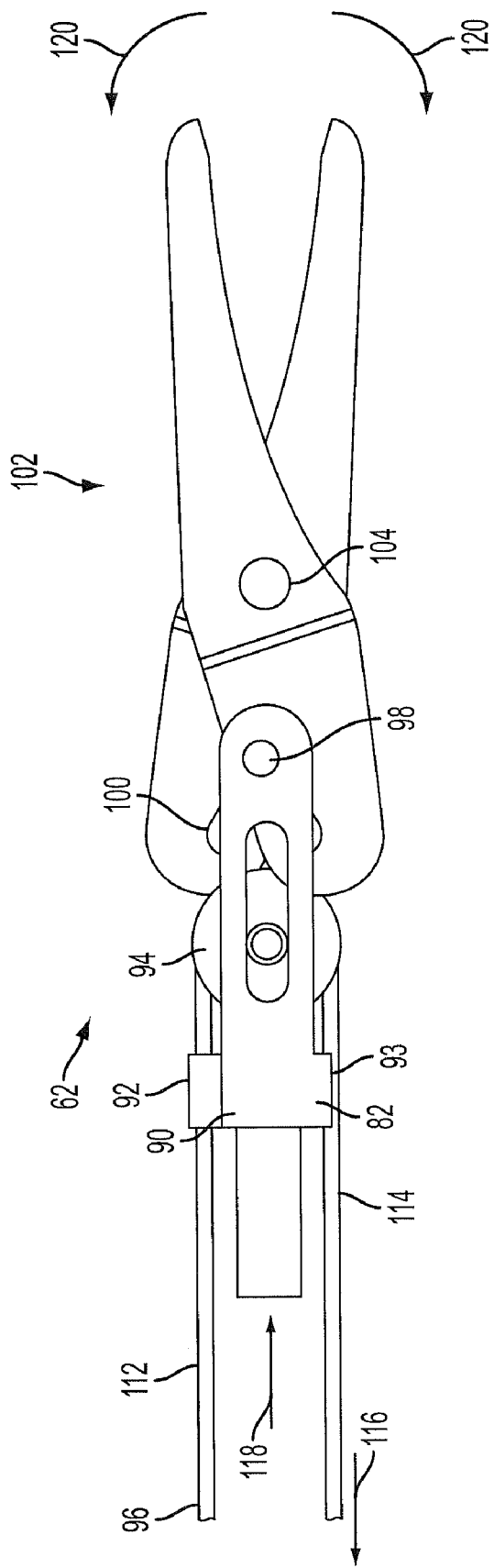
FIG. 9 is partial side plan view illustration of an actuation mechanism for the surgical tool of FIG. 6.
Figure 10:
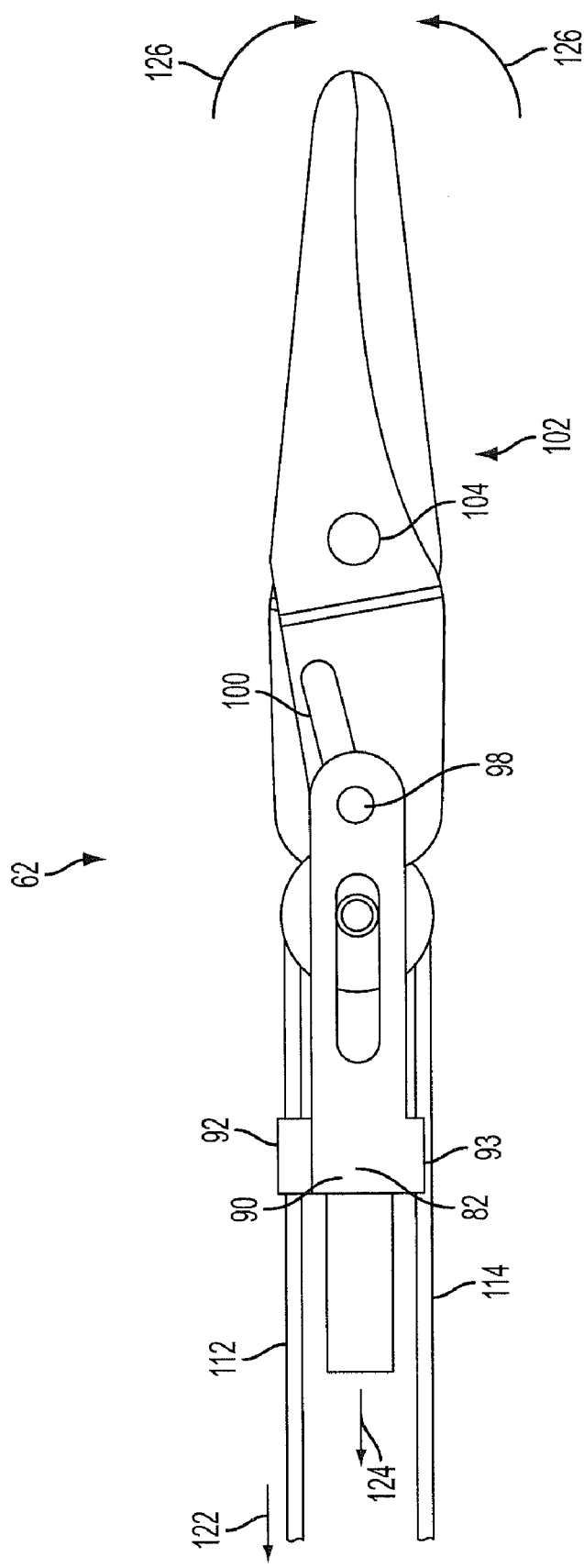
FIG. 10 is another partial plan view illustration of an actuation mechanism for the surgical tool of FIG. 6.

Referring now to FIG. 9 and FIG. 10, the operation of the scissors 102 will be described. The movement of the actuator cable 96 accomplishes the actuation of the scissors 102. The actuator cable 96 has a first portion 112 adjacent to the groove 92. The actuator cable 96 engages the pulley 94 and a second portion 114 positioned opposite the pulley 94. When the second portion 114 of actuator cable 96 is pulled, such as toward the handle 58 for example, as indicated by arrow 116 the first portion 112 of actuator cable 96 is moved toward the pulley 94. Since the clevis 82 is attached to the first portion 112 in groove 92, the clevis 82 will translate or slide within the bore 80 towards the pulley 94 in the direction indicated by arrow 118 as the cable 96 is moved about the pulley 94. This translation of the clevis 82 causes the pin 98 to apply a force to the slots 100 causing the scissors to rotate about pin 104 in the direction indicated by arrows 120. Thus, scissors 102 may be moved to the open position through the application of a single force to a single actuator cable 96. As will be discussed in more detail below, in one embodiment, the end of the first portion 112 and the end of the second portion 114 are coupled to the actuation mechanism 64, which includes means for selectively pulling on either the cable first portion 112 or the cable second portion 114.

Similarly, to close the scissors 102 as illustrated in FIG. 10, a force is applied to the actuator cable 96 first portion 112 as indicated by the arrow 122. This causes the cable 96 second portion 114 to move toward and about the pulley 94. As the cable 96 first portion 112 is away from the pulley 94, the clevis 82 slides within the bore 80 in the direction indicated by arrow 124. The translation of the clevis 82 causes the pin 98 to apply a force to the slots 100 in the opposite direction causing the scissors 102 to rotate about the pin 104 in the direction indicated by arrow 126. The rotation of the scissors 102 will continue as long as the force is applied to cable 96 second portion 114 or until the pin 98 reaches the end of slot 100. It should be appreciated that in alternate end effector device embodiments, such as forceps for example, the device may be arranged to have a predetermined closing gap by adjusting the length of the slot 100.

It should be appreciated that the components used in the end effector 62 and the tool portion 36 are compatible with medical operations. For example, such materials may be biocompatible and capable of being sterilized for example. These materials include, but are not limited to 303 stainless steel, 316 stainless steel, and 17-4 stainless steel for example.

It should further be appreciated that the end effector 62 provides a number of advantages in simplifying and reducing the size of surgical tools. The end effector 62 may be actuated between an open and a closed position using a single actuator cable 96 with a single pulley 94. Further, the end effector 62 may be actuated without requiring a return spring to move the scissors 102 to the open position. This allows the scissors 102 to be actuated in both directions allowing the operator to open the scissors in the event the scissors lock or stick in the closed position.

Figure 11:
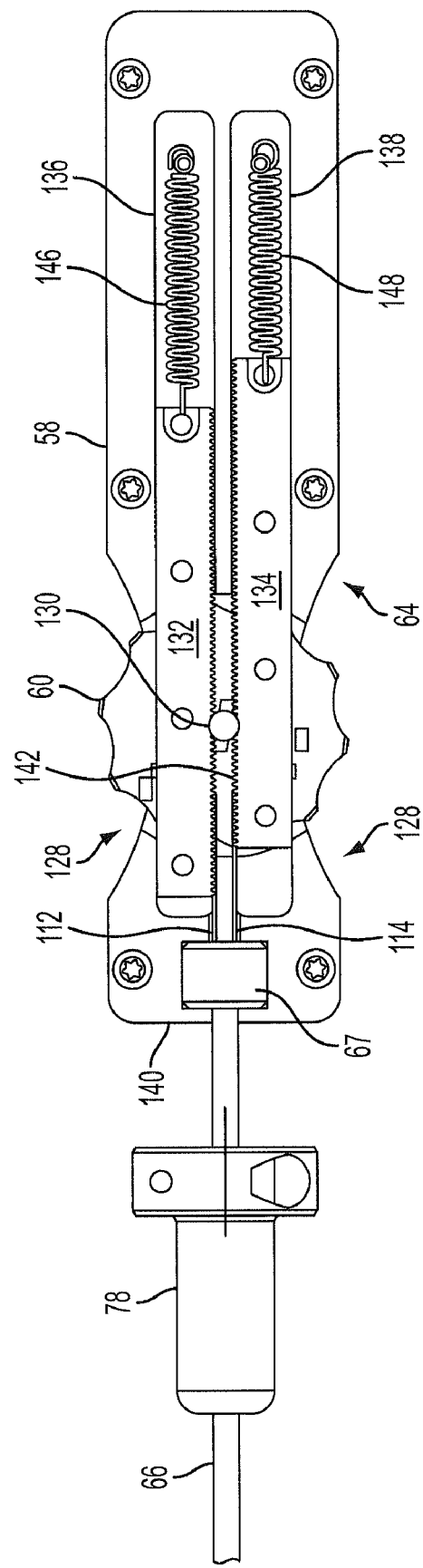
FIG. 11 is a partial side sectional view illustration of the handle portion of the surgical tool of FIG. 4.

Turning now to FIG. 11, the handle 58 and actuation mechanism 64 will be discussed. In the exemplary embodiment, the handle 58 is generally cylindrical in shape to allow the handle 58 to be comfortably held by a surgeon during the procedure. The handle 58 may be made from a suitable plastic material, such as polyphenylsulfone or polyaryletheretherketone (PEEK) for example. In the exemplary embodiment, the handle 58 is formed in two parts to facilitate manufacturing and assembly. The two halves are held together using fasteners, such as bolts, screws or adhesive for example. In the exemplary embodiment, the handle 58 includes a recess area 128 that facilitates the operator's access to the actuation knob 60 without having the actuation knob 60 extending beyond the outer diameter of the handle 58. This provides advantages in allowing the operator easy access to the actuation knob 60 while minimizing inadvertent contact with the actuation knob 60 causing an unintended actuation of the end effector 62.

In the exemplary embodiment, the handle 58 includes a pair of knobs 60 coupled to a pinion 130. The pinion 130 is secured and coupled for rotation to the handle 58. The pinion 130 includes gear teeth that engage gear teeth on a pair of rack members 132, 134. The rack members 132, 134 are arranged in recesses 136, 138 respectively in the handle 58. The recesses 136, 138 allow the rack members to move linearly within the handle 58. It should be appreciated that since the racks are located on opposite sides of the pinion 130, the rack members 132, 134 move in opposite directions when the knob 60 is rotated. Optional springs 146, 148 may be coupled to the rack members 132, 134 to maintain tension on the assembly.

The sheath 66 is coupled to the handle end 140. In the exemplary embodiment, the sheath is coupled to the handle 58 by a collar 67 that is captured in a recess between the handle 58 halves. The cable 96 first portion 112 and the second portion 114 extend from the end effector 62 through the sheath 66 and enter the handle 58 at the end 140. The end of the cable 96 first portion 112 couples to the rack member 132, while the end of the cable 96 second portion 114 couples to rack 134. In the exemplary embodiment, the rack members 132, 134 include a transverse opening 142. The ends of cable 96 enter the opening 142 in each respective rack 132, 134 whereupon they are captured by a setscrews 144, 147 respectively. The cable 96 ends may also be attached to the racks 132, 134 by other means, such as by crimping, welding or bonding for example.

During operation, the rotation of knobs 60 causes the pinion 130 gear teeth to engage the gear teeth on the racks 132, 134. The rotational movement on the knobs 60 is thus converted into linear motion of the racks 132, 134. The movement of the racks 132 in turn causes one of the first portion 112 or the second portion 114 to be pulled. In the exemplary embodiment illustrated in FIG. 11, the rotation of the knobs 60 in the clockwise direction causes the rack 132 to move away from the end 140, and correspondingly away from the end effector 62. Since the cable 96 first portion 112 is coupled to the rack 132, the cable first portion 112 is thus pulled causing the actuation of the end effector 62 to the closed position, as is illustrated in FIG. 10. Conversely, when the knob 60 is rotated in the opposite direction (counter-clockwise when viewed as in FIG. 11), the rack 134 is moved away from the end 140. This in turn causes the cable 96 second portion 114 to be pulled causing the end effector 62 to move to the open position as illustrated in FIG. 9. Thus, by rotating the knobs 60, the actuation of the end effector 62 may be effected.

Figure 13:
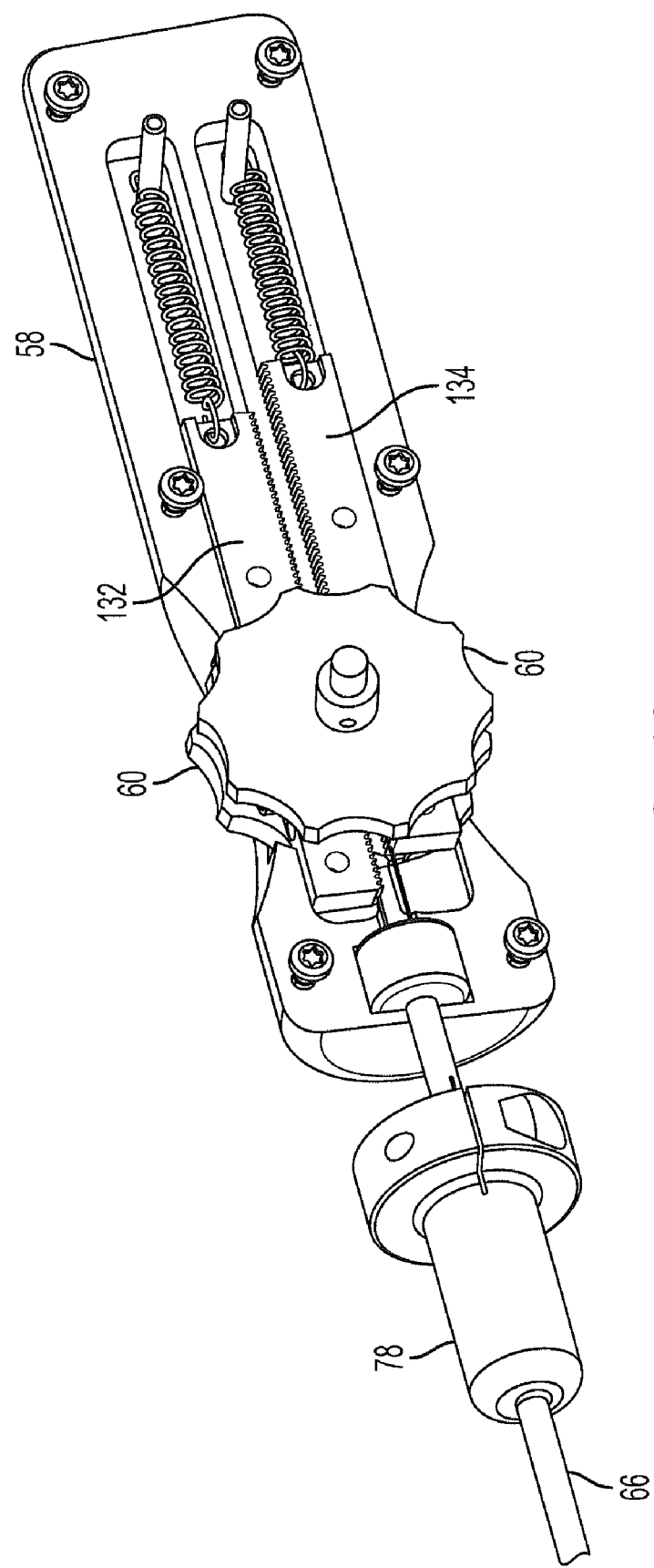
FIG. 13 is another partial perspective view illustration of the handle portion of FIG. 11.

A collar 78 is mounted to the sheath 66 adjacent the handle 58. The collar 78 is movable between a first position illustrated in FIG. 13 and a second position illustrated in FIG. 14.

Figure 7:
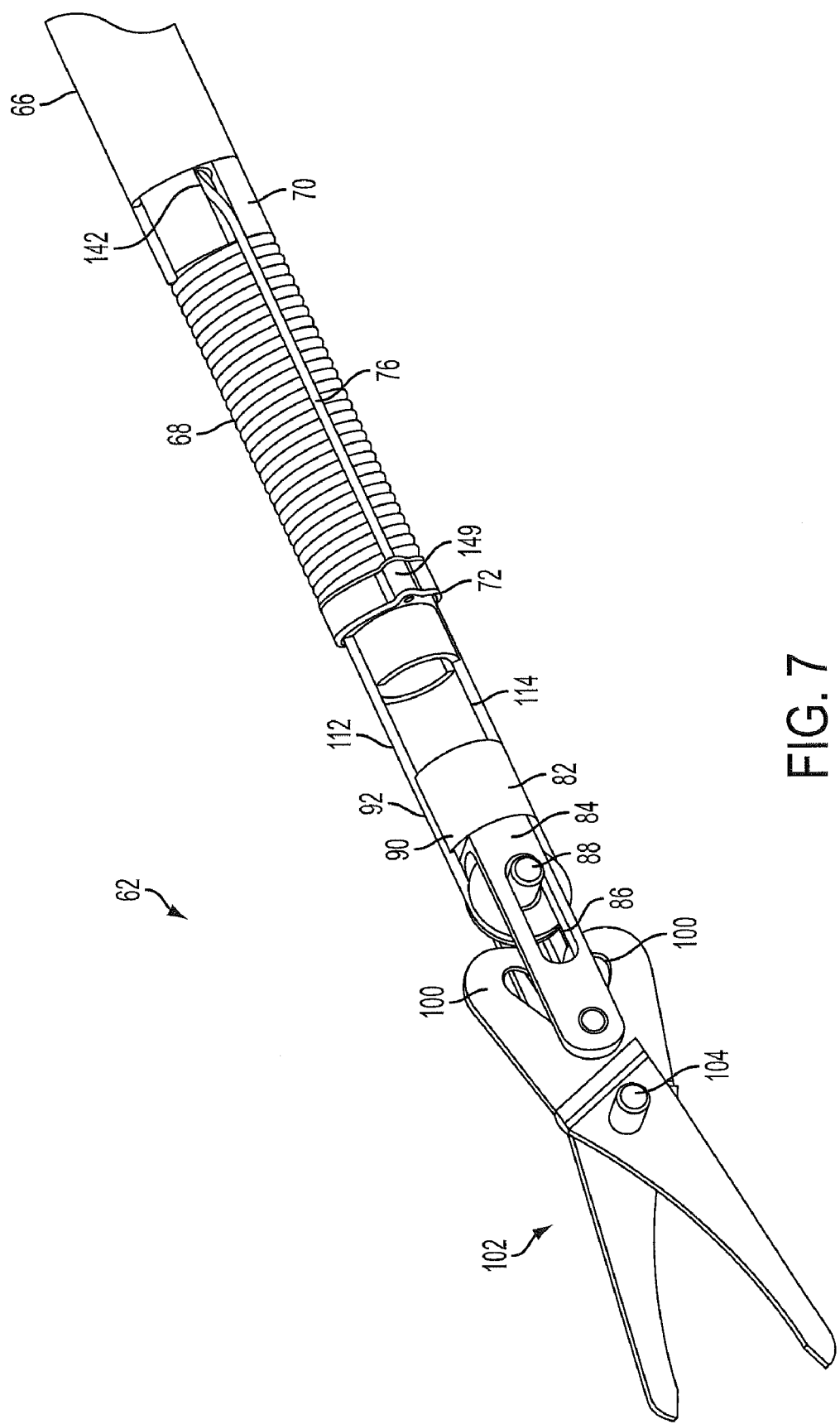
FIG. 7 is another partial perspective view illustration of the surgical tool of FIG. 6 with a shaft member removed.
Figure 8:
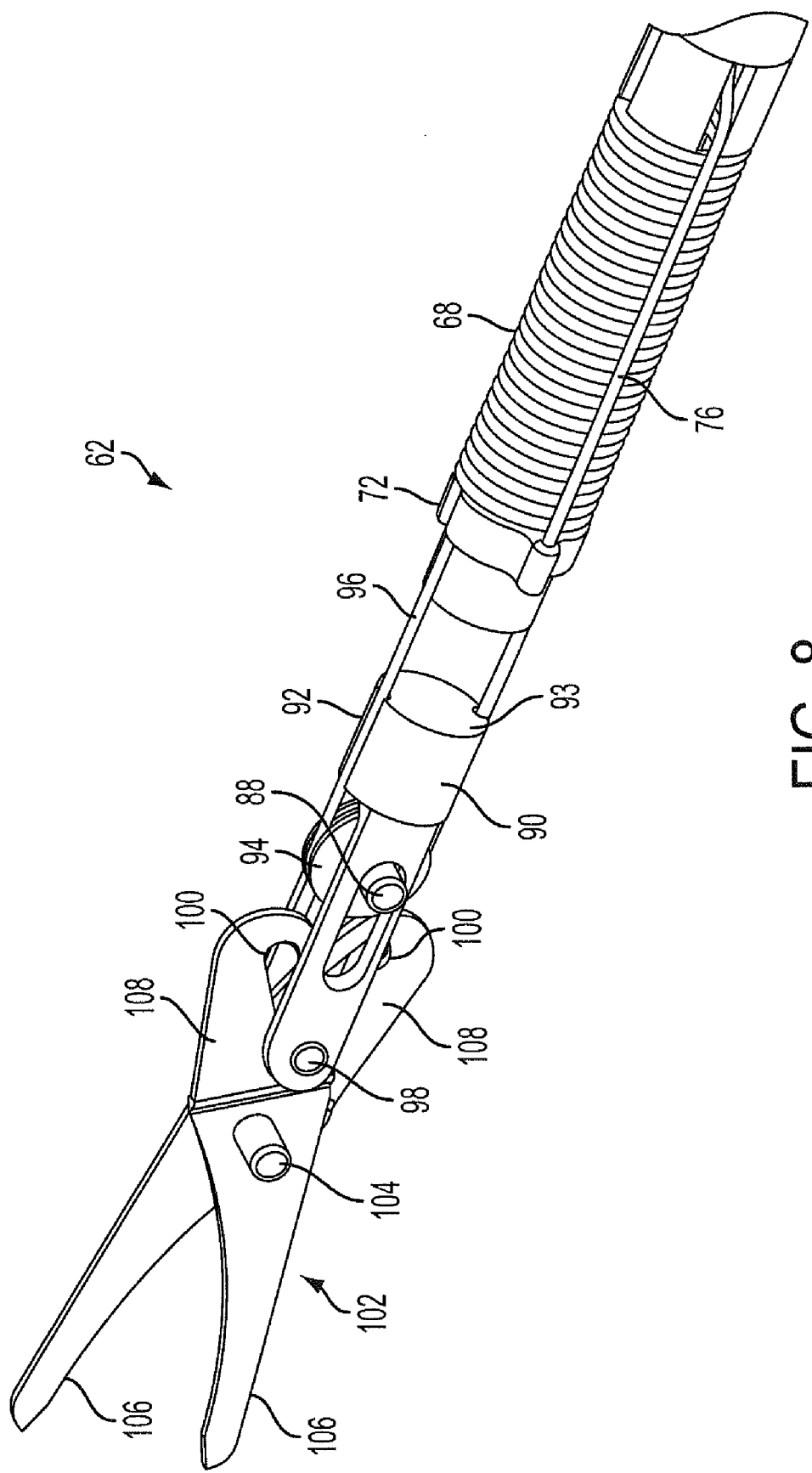
FIG. 8 is a reverse partial perspective view illustration of the surgical tool of FIG. 7.

As discussed above, the cable 76 is coupled to the collar 78. The cable 76 extends from the collar 78 through the interior portion of the sheath 66 to the terminator tip 70 (FIG. 7). The terminator tip 70 includes an opening 142 that allows the cable 76 to exit the interior of the sheath 66. After the cable 76 exits the opening 142, the cable 76 extends over the outside of the flexible member 68 and attached to the terminator tip 72 at boss 149. In the exemplary embodiment, the cable 76 is laser welded to the boss 148.

Figure 14:
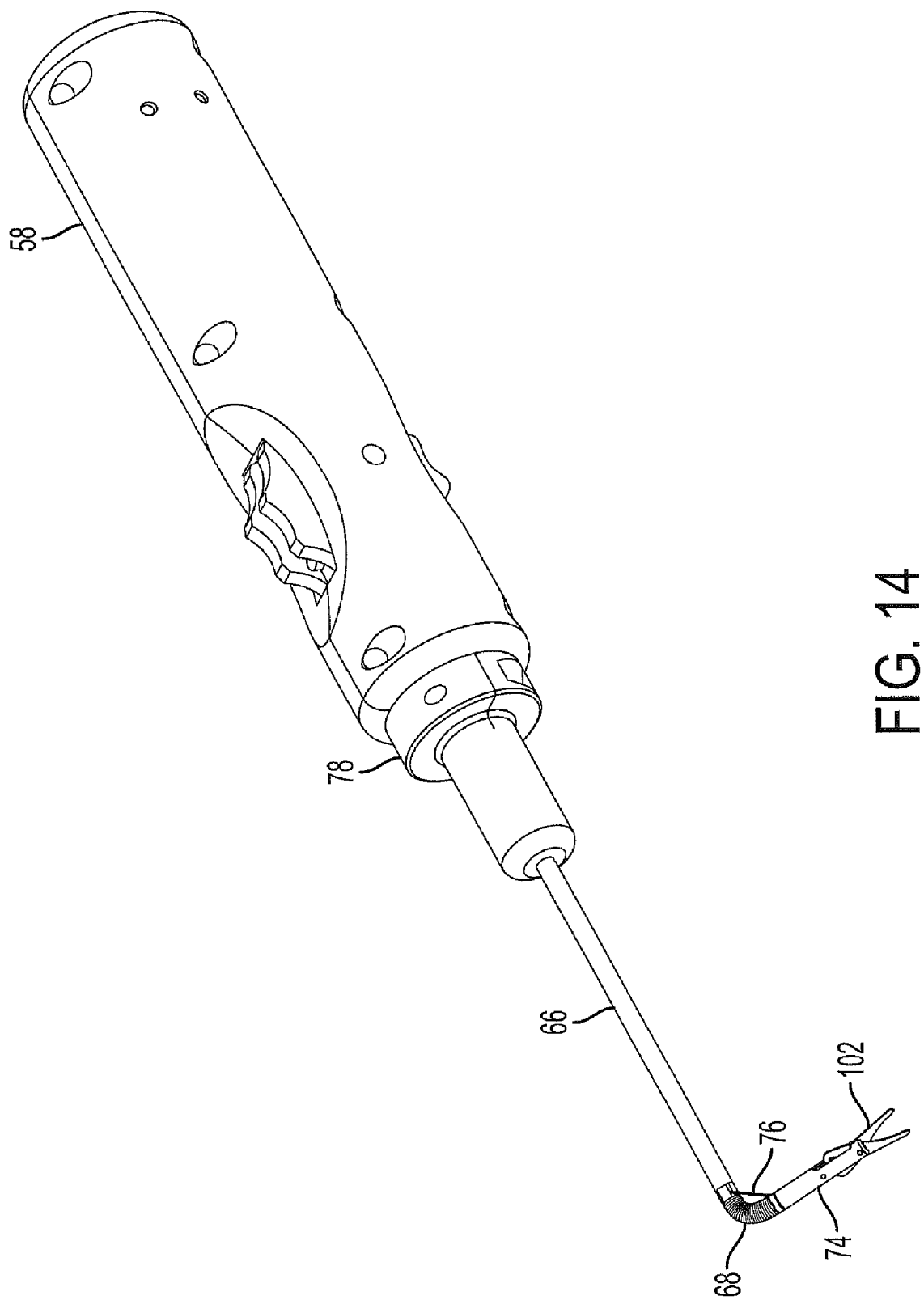
FIG. 14 is a perspective view illustration of the surgical tool of FIG. 3 with the end portion rotated relative to the handle portion.
Figure 15:
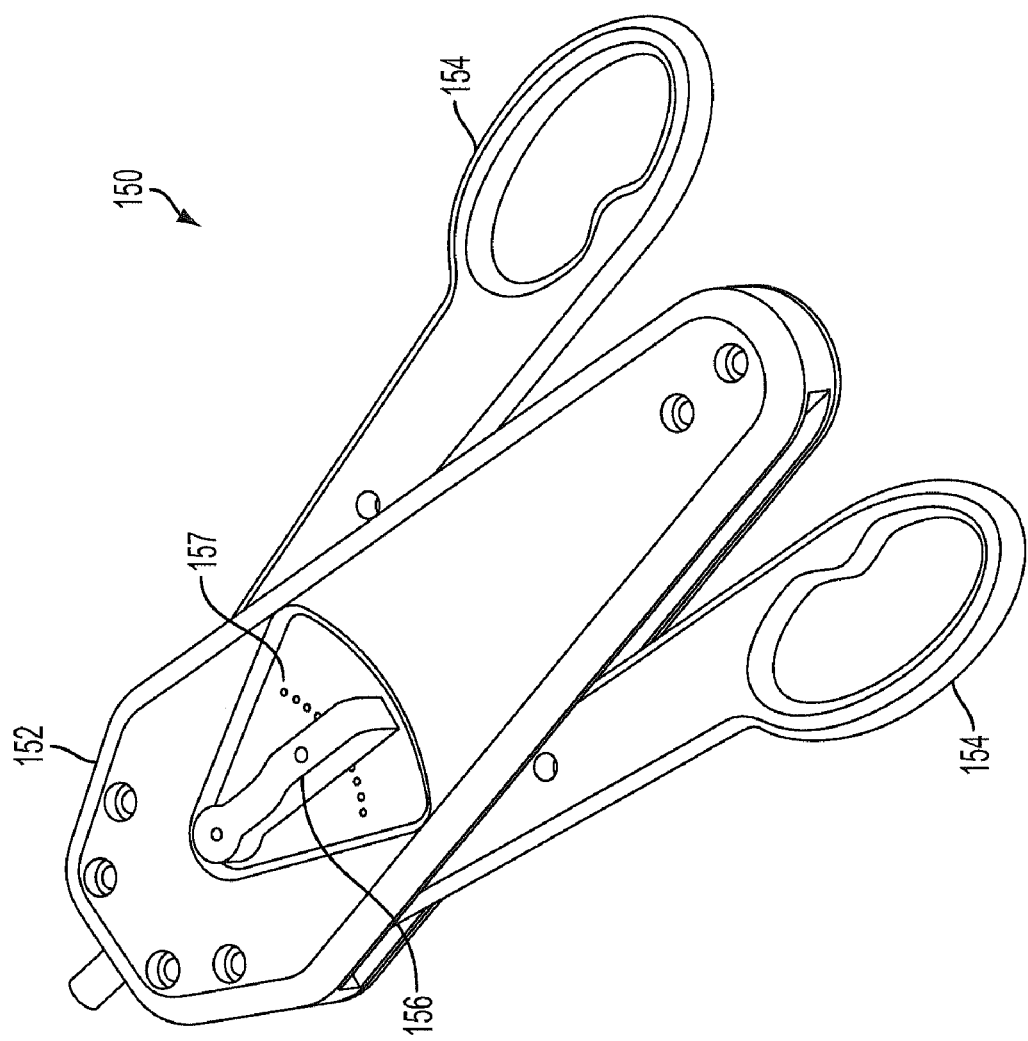
FIG. 15 is a perspective view illustration of another embodiment of a handle portion for use with the surgical system of FIG. 3.
Figure 16:
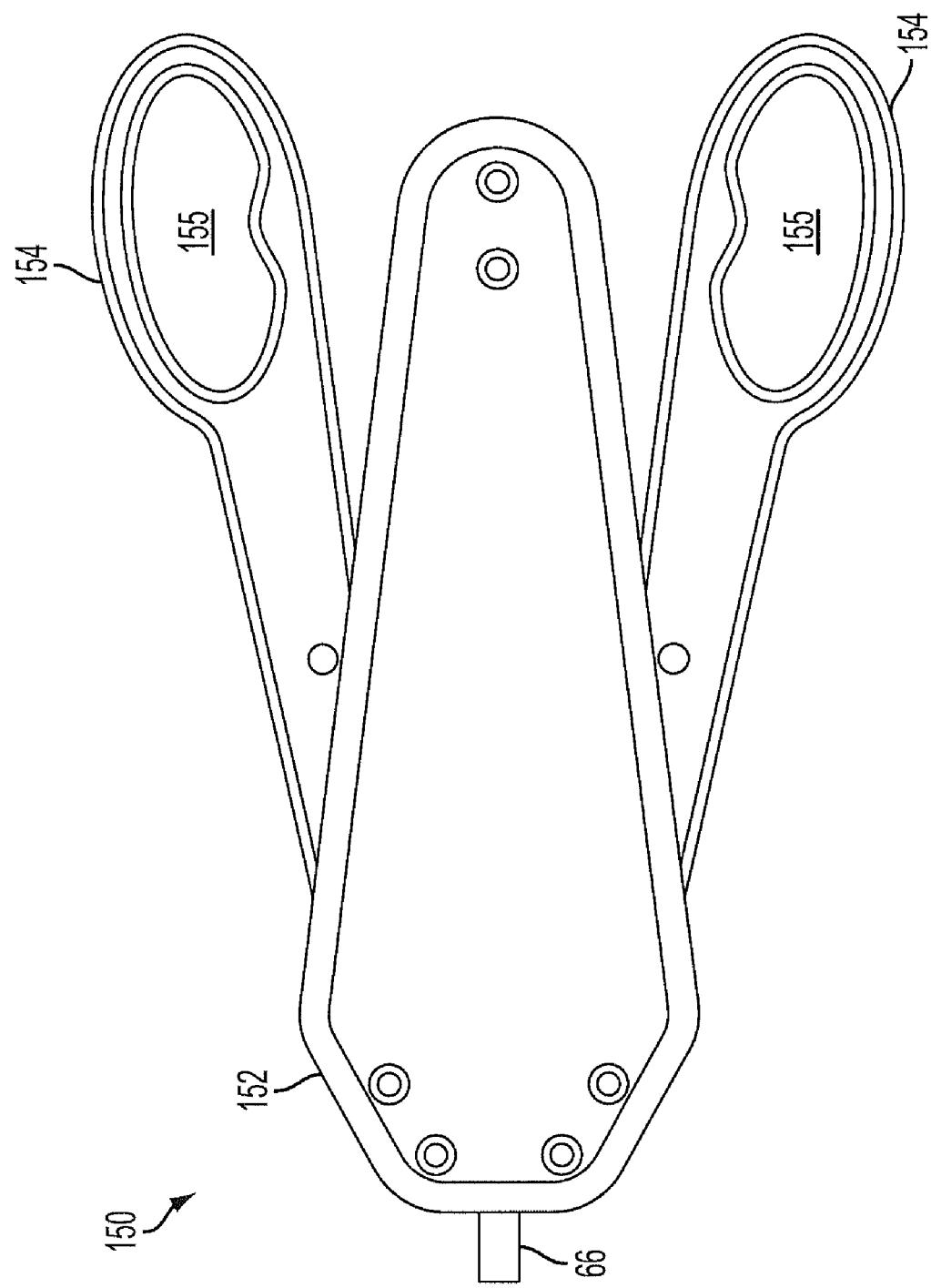
FIG. 16 is a bottom plan view illustration of the handle portion of FIG. 15.
Figure 17:
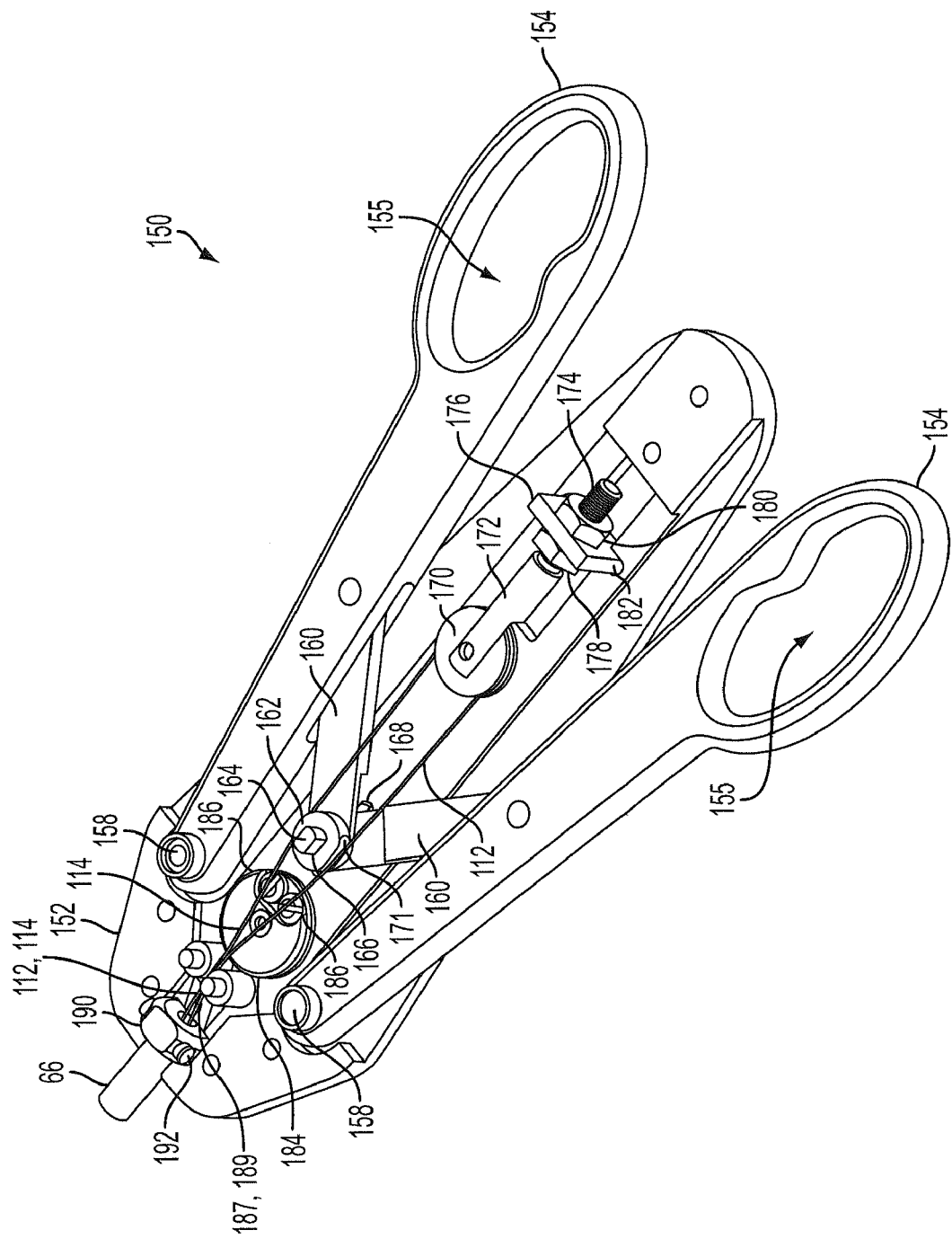
FIG. 17 is a perspective view illustration of the handle portion of FIG. 15 with a portion of a body removed.
Figure 18:
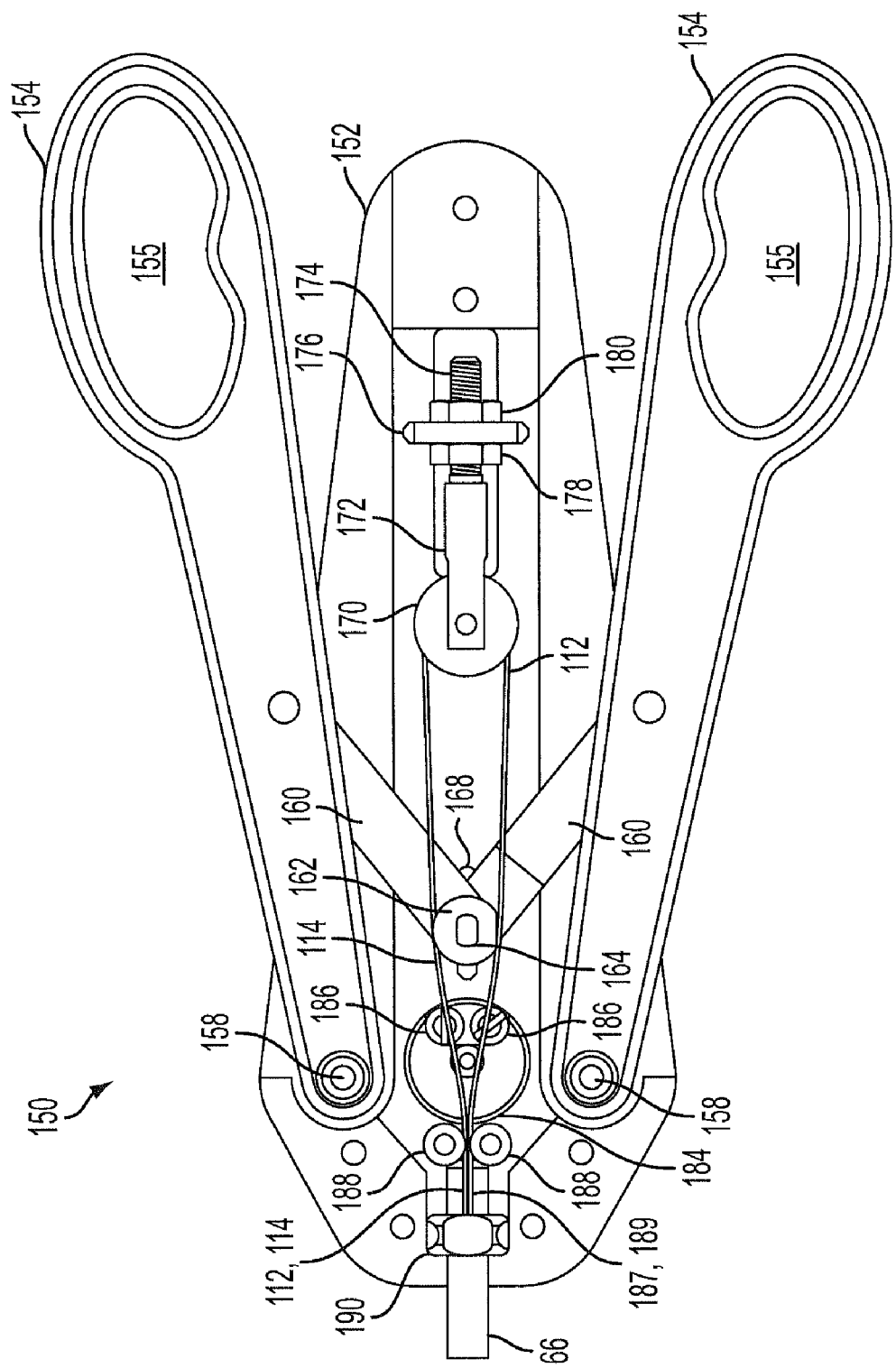
FIG. 18 is a top plan view illustration of the handle portion of FIG. 17.

When the collar 78 is moved from its initial position towards the handle 58, the cable 76 is placed under tension by moving or pulling on the boss 148. The flexible member 68 then bends under the influence of cable 76 causing the orientation of the end effector 62 to change as illustrated in FIG. 14. In the exemplary embodiment, when the collar 78 is moved to the position against the handle 58, the end effector 62 is rotated 90 degrees relative to the sheath 66.

Referring now to FIGS. 15-18, another embodiment of a handle 150 is illustrated that may be used in place of handle 58. In this embodiment, the handle 150 includes a body portion 152 with a pair of actuating handles 154. The body portion 152 may be made from a suitable material, such as polyphenylsulfone or polyaryletheretherketone for example. The actuation handles 154 include openings 155 that are sized to fit an operator's fingers. An actuation lever 156 is positioned on one side of the body portion 152. As will be discussed in more detail below, the actuation lever 156 provides the functionality of the collar 78 of the handle 58 to allow rotation of the flexible member between 0 and 90 degrees. A plurality of recesses 157 are arranged adjacent the actuation lever 156 and cooperate with a spring-loaded member (not shown) to act as a detent to hold the actuation lever 156 in place. In one embodiment, the size, position and arrangement of the body portion 152, the actuation lever 156 and the actuation handles 154 are arranged to fit comfortably in an operator's hand and allow an operator to operate the actuation lever 156 with a finger, such as a thumb for example. This provides advantages in allowing an operator to both actuate the end effector and the position of the end effector with a single hand.

The actuation handles 154 are coupled to the body 152 by pins 158. The pins 158 allow the actuation handles 154 to be rotated between an open position and the closed position (FIGS. 15-18) similar to the operation of scissors. A pair of linkages 160 are coupled on one end to the actuation handles 154 and on an opposite end to a pin 162. The pin 162 includes a protrusion 164 that extends from each end of the pin 162. The protrusion 164 includes a pair of flat surfaces 166 that are sized to fit within a slot 168 in the body 152. The pin 162 further includes a slot 171 sized to be larger than the cable 96 such that the cable 96 may freely slide past the pin 162. Opposite the slot 171, the pin 162 includes a means for attaching the cable portions 112, 114, such as but not limited to spot welding, bonding, crimping, and setscrews for example.

Adjacent the pin 162 is a first pulley 170. The first pulley 170 is attached to an arm 172 having a threaded end 174. The threaded end 174 is captured on a body 176 by a pair of fasteners 178, 180. The body 176 is captured and held in the body 152 by a pair of slots 182 formed in the body 152. The fasteners 178, 180 and the threaded end 174 cooperate to allow the pulley 170 to be moved laterally along the length of the body 152 to allow adjustment of the pulley 170 to provide a desired cable tension on the cable portions 112, 114.

Figure 12:
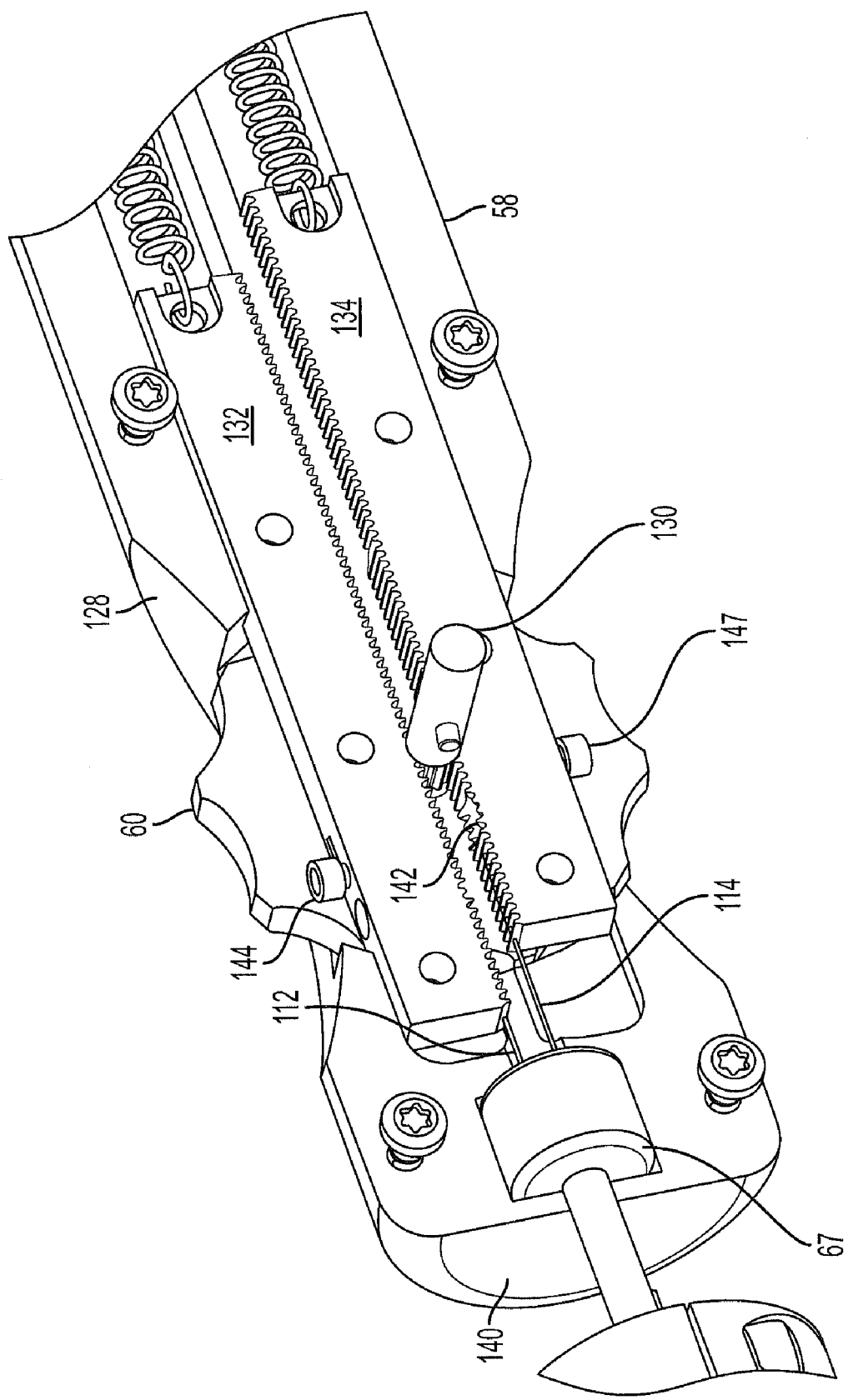
FIG. 12 is a partial perspective view illustration of the handle portion of FIG. 11.

On the opposite side of the pin 162 from the first pulley 170, a second pulley 184 is coupled for rotation to the body 152. The second pulley 184 is coupled to the actuation lever 156. The second pulley 184 includes a pair of pan-head screws 186 that are arranged to capture the ends of cables 187, 189. As will be discussed in more detail below, the opposite ends of the cables 187, 189 are coupled to the end effector 62 adjacent the flexible member 68. It should be appreciated that as the actuation lever 156 is rotated, the second pulley 184 is also rotated, pulling one of the ends of the cable 76 resulting in the movement of the flexible member 68. Adjacent the second pulley 184 a pair of rollers 188 are coupled for rotation to the body 152, the rollers 188 guide the cables 112, 114, 187, 189 as they exit the sheath and are spaced apart to allow the cables 76, 112, 114 to pass through. Similar to the embodiment illustrated in FIGS. 11-13, a collar 190 is coupled to the sheath 66. The collar 190 is captured in a slot 192 in the body 152 coupling the sheath 66 to the handle 150.

During operation, the operator sets the angle of the flexible member 68 to the desired position by rotating the actuation lever 156. In the exemplary embodiment, when the actuation lever 156 is in the middle position shown in FIG. 15, the flexible member 68 is straight. When the actuation lever 156 is rotated in either direction, the flexible member 68 bends in that direction. In the exemplary embodiment, the flexible member 68 rotates 90 degrees when the actuation lever 156 is moved to the end position and has a range of −90 degrees to +90 degrees. To actuate the end effector 62, the operator moves the actuation handles 154 in a scissor action. As the actuation handles 154 are rotated, the linkages 160 cause the pin 162 to move along the slot 168. The movement of the pin 162 results in either the cable first portion 112, or the cable second portion 114 being pulled. As discussed herein above, the pulling of cable portions 112, 114 results in the actuation of the end effector 62.

Figure 19:
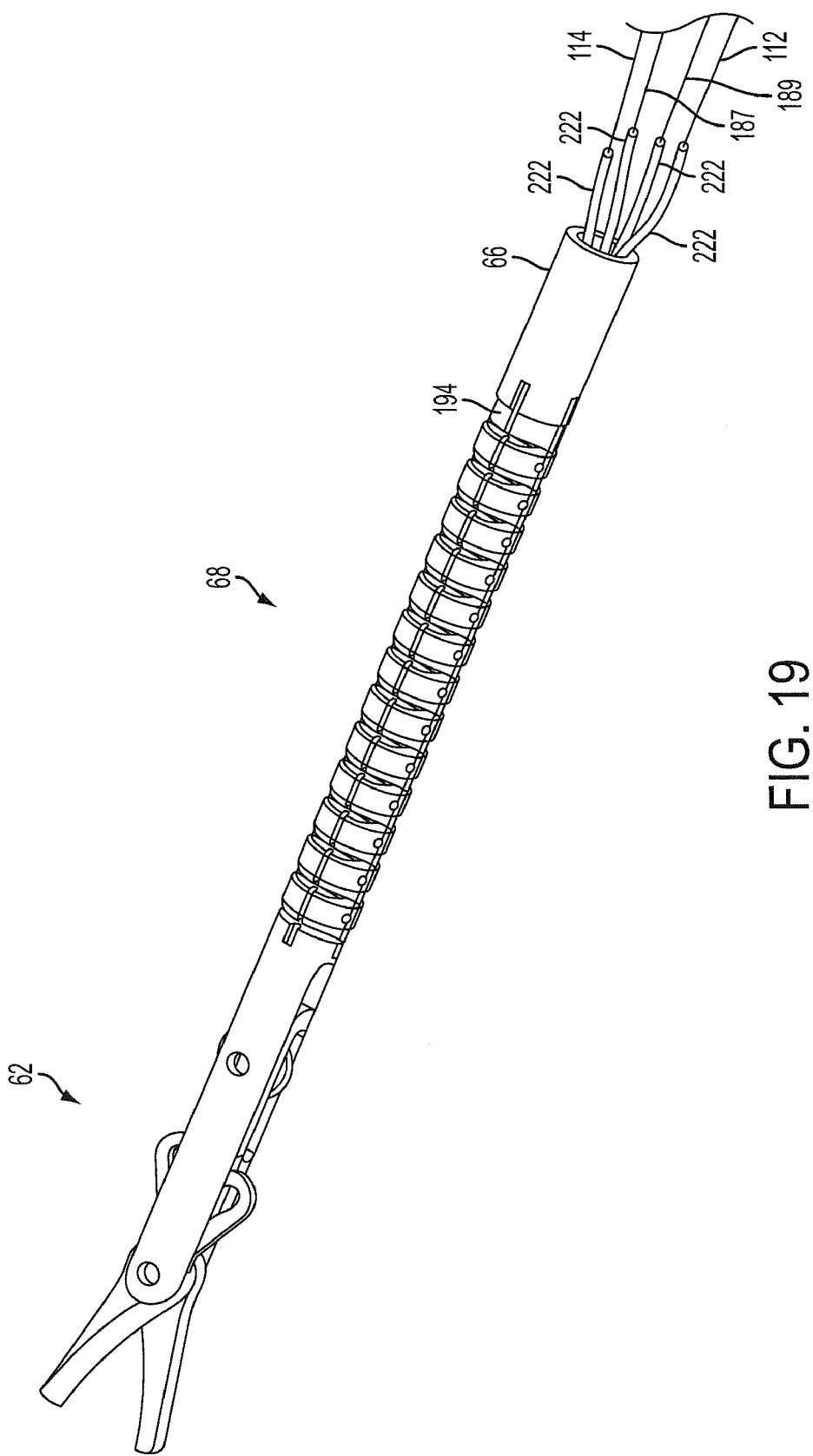
FIG. 19 is a perspective view illustration of another embodiment of a flexible member for use with the surgical system of FIG. 1, FIG. 2, or FIG. 3.
Figure 20:
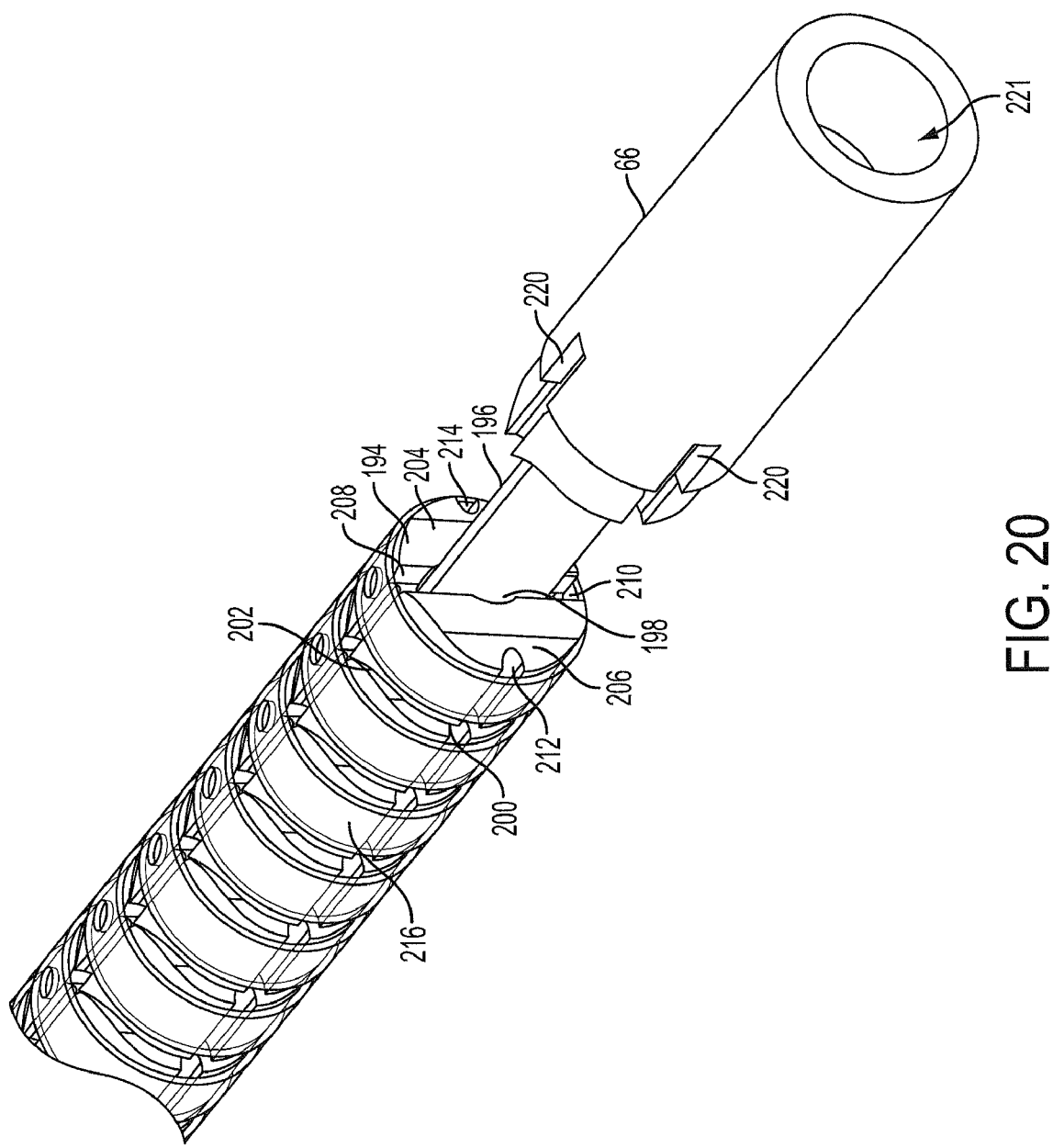
FIG. 20 is a partial perspective view illustration of the flexible member of FIG. 19 with several links removed; and, FIG. 21 is another partial perspective view illustration of the flexible member of FIG. 19.
Figure 21:
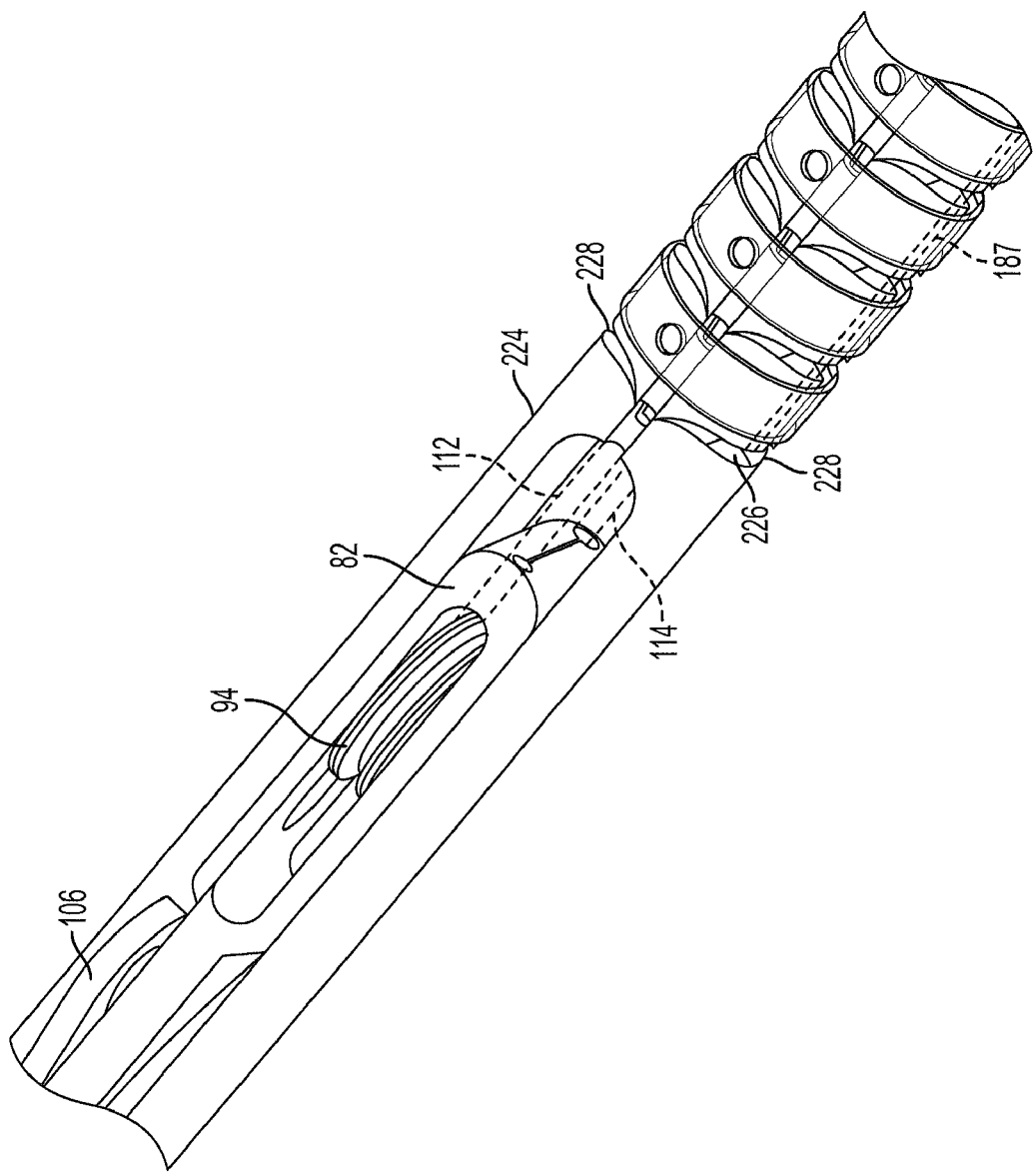

Referring now to FIGS. 19-21, another embodiment of a flexible portion 68 is shown. In this embodiment, the flexible portion 68 is arranged between the end effector 62 and the sheath 66. The flexible portion 68 is operably coupled to the handle 58, 150 to allow bending of the flexible portion 68, such that pulling on the cables 187, 189 may rotate the end effector. In some embodiments, the end effector 62 may have a greater, or a lesser, amount of rotation. In other embodiments, only one cable 187, 189 is used and the end effector 62 may only be bent in a single direction. The flexible portion 68 includes a plurality of links 194 that are disposed about a center beam 196 (FIG. 20). It should be appreciated that FIG. 20 is illustrated with several links 194 removed for clarity.

Each link 194 includes a center slot 198 that is sized to receive the beam 196. In the exemplary embodiment, the beam 196 has a generally rectangular cross-section that allows the beam to be bent in the plane perpendicular to the long side while remaining substantially rigid in the transverse direction. The beam 196 is coupled to both the sheath 66 and the clevis 224 by a suitable means. When assembled on the beam 196, each link 194 contacts, but is not fixedly coupled to the adjoining links 194, such that when the flexible portion 68 is bent, the links 194 are free to bend with the beam 196. Each link 194 further includes a first side 200 having a relief surface 202. Opposite the first side 200 is a second side 204 having a surface 206. In one embodiment, the relief surface 202 and the surface 206 are sized and shaped such that the relief surface 202 on one link 194 contacts the surface 206 on the adjoining link 194 when the flexible portion is bent to its maximum position (e.g. −90 degrees or +90 degrees). It should be appreciated that in one embodiment, each first side 200 includes two relief surfaces 202 and each second side 204 includes two surfaces 206.

The links 194 are generally cylindrical in shape. The links further include four slots 208, 210, 212, 214 that are disposed about the periphery of the link 194. The slots 208, 210, 212, 214 are substantially aligned with the longitudinal axis of the beam 196. The slots 208, 210, 212, 214 for each of the links 194 are substantially aligned to form a pathway for the cables 76, 112, 114, 187, 189. In the one embodiment, the cable 76 is arranged in either slot 212 or slot 214. In another embodiment, the cables 187, 189 are arranged in slots 212, 214 respectively. The cable portion 112 is arranged in slot 208 and the cable portion 114 is arranged in slot 210. A band 216 is disposed over the link 194 to capture the cables 76, 112, 114, 187, 189 in the slots 208, 210, 212, 214. In the exemplary embodiment, the band 216 includes an opening 218 that allows the band 216 to be fixed to the link 194, such as through tack welding for example. In the exemplary embodiment, the links 194, beam 196 and bands 216 are made from a biocompatible material, such as stainless steel or carbon steel for example. In other embodiments, the band 216 is removed and the cables 76, 112, 114, 187, 189 are captured in the slots 208, 210, 212, 214 by another method, such as by crimping the slots 208, 210, 212, 214 for example. In another embodiment, tubes 222 which are extended from the sheath 66 through the slots 208, 210, 212, 214 and a shrink wrap material is formed over the flexible portion 68.

The flexible portion 68 is coupled on one end to the sheath 66. In one embodiment, the sheath 66 includes a plurality of slots 220 disposed on one end. The slots 220 are sized and arranged to align with the slots 208, 210, 212, 214 in the links 194. The slots 220 allow the cables 76, 112, 114, 187, 189 to enter into the substantially inner portion 221 of the sheath 66. In one embodiment, the cables 76, 112, 114, 187, 189 are arranged in low friction tubes 222 to prevent binding as the cables 76, 112, 114, 187, 189 traverse the length of the sheath 66. In one embodiment, the tubes 222 are made from a plastic material, such as polytetrafluoroethylene (PTFE) for example.

The flexible portion 68 is also coupled to the end effector 62. In this embodiment, the clevis 224 includes an end 226. The end 226 includes a surface 228 that is shaped substantially the same as the surface 206 of link 194. The clevis 224 further includes a pair of slots 230 arranged and sized to align with the slots 208, 210. The slots 230 allow the cable portions 112, 114 to enter the clevis 224 and engage the pulley 94 as described herein above. The ends of the cables 187, 189 are fixedly attached to the clevis 224 by a suitable means such as tack welding or crimping for example. It should be appreciated that the cables 112, 114, 187 are illustrated in FIG. 20 in a dashed line for clarity. When one of the ends of the cables 187, 189 is pulled by the rotation of the actuation lever 156, the clevis 224 places a bending moment on the flexible member 68 causing the beam 196 to bend.

The embodiments described herein provide for a surgical tool that may provide an improved solution for reducing the cost, size and complexity of surgical tools used in minimally invasive medical procedures. The surgical tool provides for the actuation of an end effector in two directions with a single cable. This may eliminate the need for a return spring and avoids having the end effector become stuck in the closed position. Further, the surgical tool provides additional advantages. The surgical tool includes a mechanism for rotating the orientation of the end effector, for example. The surgical tool may also be incorporated in a variety of surgical systems, including a robotic, a direct drive or a hand-held system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, front, rear, top, bottom etc. do not denote any orientation, order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A surgical tool comprising:
   an end effector having a first pivot, said end effector having an operable portion on a first side of said first pivot, and a first slot on a second side opposite said first pivot;
   a clevis slidably coupled to said first slot, said clevis having a second slot;
   a single pulley adjacent said second side, said pulley being rotationally coupled to said second slot; and,
   a first cable coupled to one side of said clevis adjacent said pulley and engaging said pulley, wherein said end effector moves between an open and closed position in response to movement of said first cable; wherein further comprising a shaft having a bore, wherein said clevis is arranged within said bore; wherein said pulley further includes a second pivot coupled to the shaft; wherein the shaft includes an opening between and substantially perpendicular to the first pivot and the second pivot; and the clevis is movably coupled to the bore between a first position and a second position, wherein said second side is positioned within the bore when the clevis is in the first position and a portion of the second side is within the opening when the clevis is in the second position.

2. The surgical tool of claim 1 wherein said clevis includes a first arm, said pulley being arranged adjacent said first arm.

3. The surgical tool of claim 1 wherein said operable portion includes a blade portion.

4. The surgical tool of claim 1 wherein said second slot is substantially parallel to the length of said shaft.

5. The surgical tool of claim 4 wherein said clevis includes a body portion arranged on an end opposite the end effector.

6. The surgical tool of claim 5 wherein said body includes a pair of opposing grooves, said grooves being sized to receive said first cable.

7. The surgical tool of claim 6 wherein said first cable is fixedly coupled to one of said pair of opposing grooves.

8. The surgical tool of claim 4 wherein said clevis further includes a pair of arms extending from said body, the second slot being arranged in one of said pair of arms.

9. The surgical tool of claim 8 wherein said pulley is disposed between said pair of arms.

10. The surgical tool of claim 1 wherein said first slot is substantially straight and disposed on an angle relative to the length of the shaft.

11. The surgical tool of claim 10 wherein said end effector is a forcep.

12. The surgical tool of claim 10 wherein said end effector is a grasper.

13. The surgical tool of claim 10 wherein said end effector is a punch.

14. The surgical tool of claim 10 wherein said end effector is a fan-style retractor.

15. The surgical tool of claim 1 further comprising a spring member coupled to an end of said shaft opposite said end effector.

16. The surgical tool of claim 15 further comprising a termination tip between said spring member and said shaft.

17. The surgical tool of claim 16 further comprising a second cable coupled to said termination tip, said spring member being configured to bend in response to said second cable being moved.

* * * * *